United States Patent [19]

Ryan

[11] Plant 4,721

[45] May 19, 1981

[54] IMPATIENS PLANT NAMED DELAWARE

[76] Inventor: John J. Ryan, 39877 Sundale Dr., Fremont, Calif. 94538

[21] Appl. No.: 144,163

[22] Filed: Apr. 28, 1980

[51] Int. Cl.[3] ..... A01H 5/00
[52] U.S. Cl. ..... Plt./68
[58] Field of Search ..... Plt./68

*Primary Examiner*—Robert E. Bagwill
*Attorney, Agent, or Firm*—James R. Cypher

[57] ABSTRACT

This invention relates to a new and distinct variety of New Guinea Impatiens plant, known by the cultivar name Delaware, a seedling resulting from the cross pollenation of unpatented pistil parent and patented pollen parent "Mohawk"; and distinguished from Mohawk by its distinctly deeper red-purple color tone, definite yellow-green foliage variegation, lighter green larger foliage, semi-dwarf plant size, and up-right, only slightly spreading growth habit.

1 Drawing Figure

BACKGROUND OF THE INVENTION

The present new variety (seedling) was discovered by me in a commercial greenhouse in Fremont, Calif., as a result of a definite breeding program to produce better and different commercial varieties of plants.

The cross pollenation of unpatented pistil parent 77-321-2 and patented pollen parent 77-342-3, Mohawk, U.S. Plant Pat. No. 4,427, granted June 12, 1979, produced a plant distinctly different than either one of its parents and it was, therefore, selected for propagation by cuttings. Repeated propagations and flowerings of my new variety through asexual reproduction by terminal or stem cuttings grown in pots in a plastic (polyethylene) greenhouse in Fremont, Calif., under normal environmental conditions show that the characteristics described come true to form and are established and transmitted through succeeding generations.

BRIEF SUMMARY

The known commercial variety to which Delaware would be closest in characteristics is its pollent parent, Mohawk, but Delaware is distinctly different than Mohawk in the following characteristics:

1. The foliage of Mohawk is dark green with no variegation while the foliage of Delaware is a lighter green and has definite yellow-green variegation. Delaware's foliage is also slightly larger than Mohawk's.
2. The flower color of Delaware differs from Mohawk in that the red-purple color tone is much deeper.
3. Delaware is a smaller plant than Mohawk.
4. Delaware is slower to bloom than Mohawk and is never quite as floriferous.

DESCRIPTION OF PHOTOGRAPH

The accompanying color photograph illustrates the overall appearance and form of the plant as well as the nature and color of its flowers and foliage; the color rendition being as nearly true as is reasonably possible to obtain by conventional photographic procedures. The photograph was taken under intensive light conditions. Under less intensive light, the flower color is slightly darker.

DETAILED DESCRIPTION

Referring to the botanical details of my new variety, the following detailed description is based on observations made on Mar. 9, 1980. All plants were grown under normal environmental conditions in greenhouses. Color readings were taken during daylight hours in full sun, and all colors are based on the Royal Horticultural Society Colour Chart.

I. Plant:
- *Name.*—Delaware.
- *Origin.*—Seedling of the cross pollenation of the unpatented pistil parent 77-321-2 and the patented pollen parent 77-342-3, Mohawk, U.S. Plant Pat. No. 4,427, granted June 12, 1979.
- *Form.*—Upright to spreading.
- *Height to flowering.*—25 cm.
- *Growth.*—Fast, yet compact, if not crowded.
- *Type of cuttings.*—Terminal or stem.
- *Rooting time.*—Typical, 10–14 days.
- *Rooting habit.*—Fast, dendritic.

II. Foliage:
- *Arrangement.*—Lower leaves of any break opposite (usually one set); upper foliage of any break whorls of 3 to 6 (any over 4 seem to be a compressed internode with 2 nodes pushed together).
- *Shape.*—Elliptical to oblanceolate.
- *Tip.*—Acuminate.
- *Base.*—Attenuate.
- *Margin.*—Serrulate.
- *Veination.*—Pinnate.
- *Size.*—Blade and petiole 9.5 cm to 15.5 cm; length of blade 8 cm to 14 cm; width of blade at widest point 3 cm to 5 cm.
- *Surface.*—Glabrous.
- *Variegation.*—High light and age of cutting increase variegation; whereas low light and high fertilization reduce variegation and increase leaf size.
- *Color.*—1. Petiole—138D with striated red 51A. 2. Veins—a. Upper 50B b. Lower 138D 3. Leaf—a. Upper 137A b. Lower 138B 4. Variegation—a. Edge 137A b. Middle 154A until it is distinct enough (extremely small band) c. Center 6A.

III. Stem:
- *Color.*—181B on aged stem in sun.
- *Internode.*—1. Length—Short if not crowded. 2. Size—Moderate.
- *Node expanded (relative to internode).*—Slightly expanded.
- *Breaking action.*—Good.

IV. Flower:

*Form.*—Typical.

*Borne.*—End of branches, terminal.

*Blooming habit.*—1. Relative number—above average. 2. Time to flowering—Early but longer than Mohawk. 3. Longevity—Typical, 3 to 5 days.

*Size of mature flower.*—First flower on a plant may be small. 1. Length—5.5 cm to 6.0 cm. 2. Width—5.0 cm to 5.5 cm. 3. Spur—5.0 cm to 6.0 cm.

*Color.*—Lightens under high light. 1. Eye—67B to 68C-68D at very center. 2. Middle—66B. 3. Edge—66B. 4. Pedicel—46C. 5. Spur—46A.

V. Reproductive organs:

*Stamen.*—

| | |
|---|---|
| 1. Anthers<br>2. Filaments<br>3. Pollen | Typical, fused hood over pistil--colored hood 50A.<br>a. Color--158B to 158C<br>b. Abundance--Plenty |

*Pistils.*—

| | |
|---|---|
| 1. Style<br>2. Ovaries | Typical |

I claim:

1. A new and distinct form of Impatiens plant as described and illustrated, known by the cultivar name Delaware.

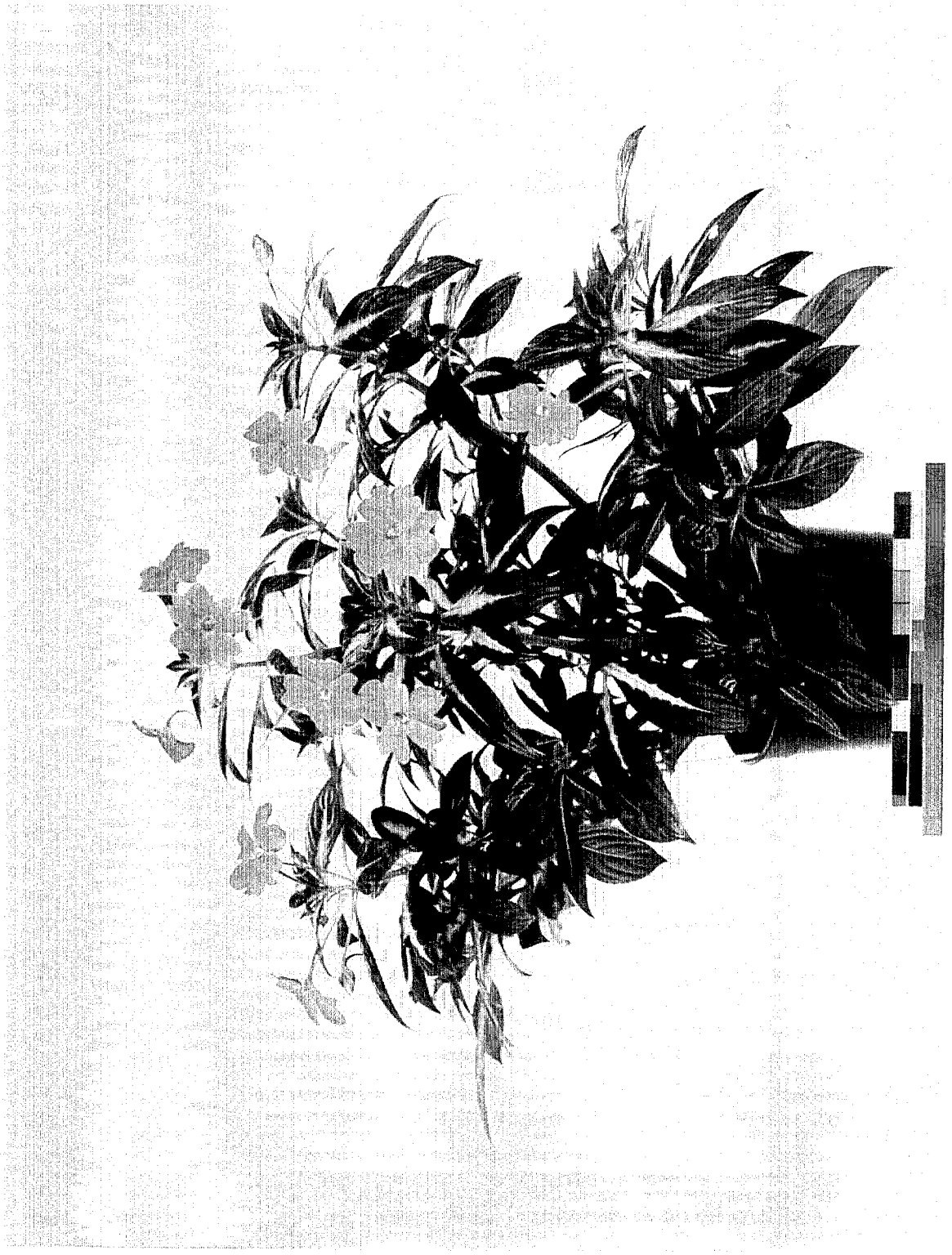

* * * * *